United States Patent [19]

Smith et al.

[11] Patent Number: 4,502,338

[45] Date of Patent: Mar. 5, 1985

[54] TRIAXIAL APPARATUS FOR TESTING PARTICULATE MATERIAL AND METHOD OF USING THE SAME

[75] Inventors: David L. O. Smith; Robert A. Lohnes, both of Ames, Iowa

[73] Assignee: Iowa State University Research Foundation, Inc., Ames, Iowa

[21] Appl. No.: 494,801

[22] Filed: May 16, 1983

[51] Int. Cl.³ ............................................. G01N 3/08
[52] U.S. Cl. ...................................... 73/819; 73/820; 73/825; 73/826
[58] Field of Search ................. 73/819, 820, 822, 825, 73/826

[56] References Cited

U.S. PATENT DOCUMENTS 2,531,083 11/1950 Smith .
2,711,644 6/1955 Myers .
3,608,367 9/1971 Karol .
3,616,685 11/1971 Strom ................................... 73/819
3,890,830 6/1975 Dyck .
4,122,704 10/1978 Lutenegger et al. .

Primary Examiner—Anthony V. Ciarlante
Attorney, Agent, or Firm—Zarley, McKee, Thomte, Voorhees & Sease

[57] ABSTRACT

A triaxial cell apparatus for conducting constant lateral stress tests, constant volume tests and zero lateral strain tests on particulate materials. Pressure and volume measuring devices are in communication with a flexible inner specimen cylinder and with a rigid outer cylinder mounted on the apparatus frame. A control panel permits the compressed air confining stress to be regulated as axial stress is applied through a piston assembly having the same cross-sectional area as the specimen cylinder. The different tests are conducted by various combinations and hookups between the pressure and volume measuring devices and the control panel. The tests can be performed on a specimen so that the stress history of that material may be determined for later use in confining structure design.

19 Claims, 5 Drawing Figures

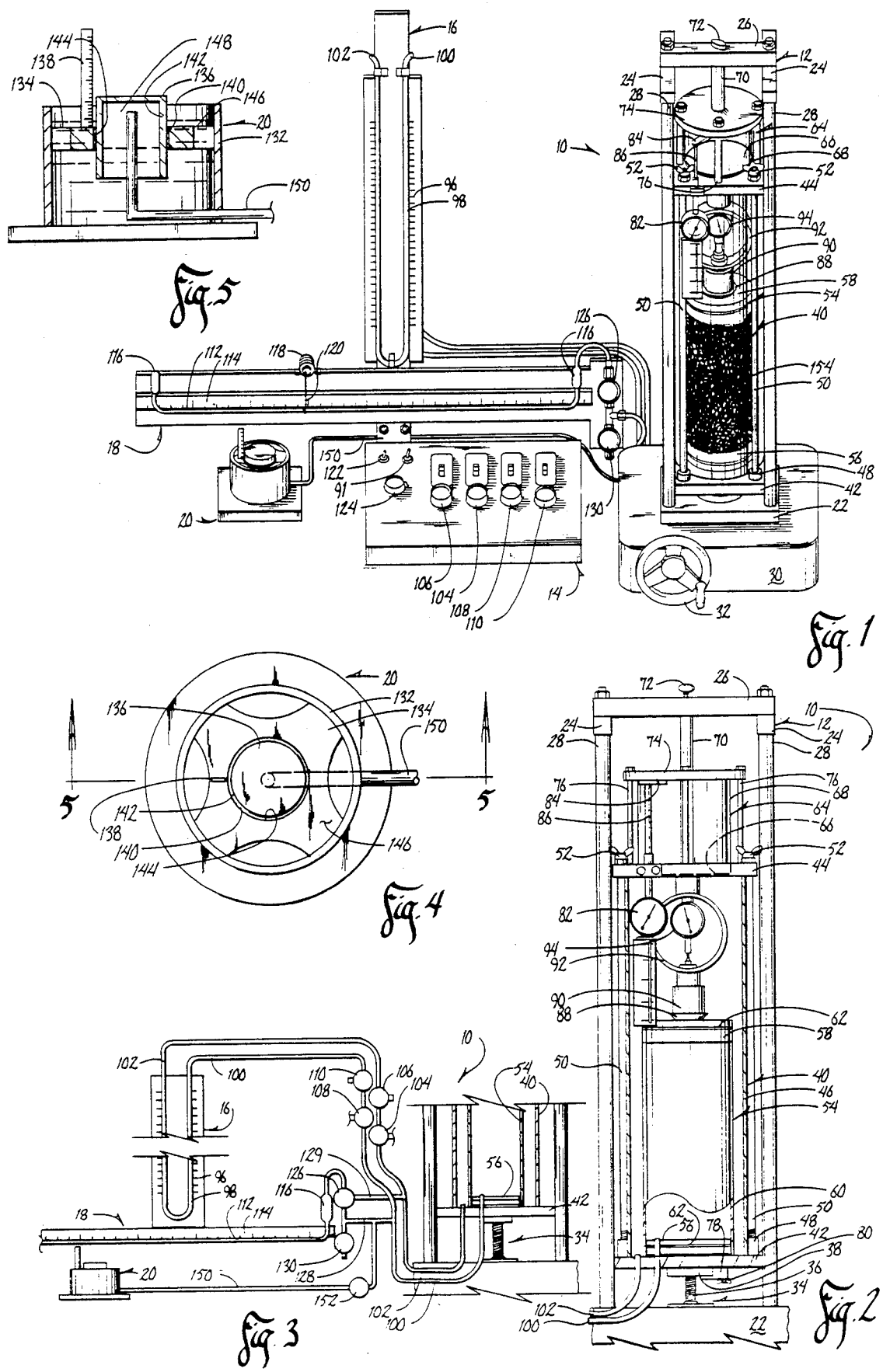

TRIAXIAL APPARATUS FOR TESTING PARTICULATE MATERIAL AND METHOD OF USING THE SAME

BACKGROUND OF THE INVENTION

It is well known that the stress-strain characteristics of soil are dependent upon the stress paths used to test the soil. For example, if a triaxial test specimen is subjected to compression loading, i.e., increasing vertical stress while holding lateral stress constant, the failure stress will be much higher than if the specimen is subjected to compression unloading, i.e., decreasing lateral stress while holding vertical stress constant. Different results will also be obtained by subjecting the specimen to extension unloading, i.e., increasing lateral stress while holding vertical stress constant, or to extension loading, i.e., decreasing vertical stress while holding lateral stress constant. Other bulk solids such as agricultural grains, coal, cement powder, ores and polyethyene pellets will exhibit a similar sensitivity of stress-strain behavior to the method of loading.

The finite element method of determining stress-strain relationships is important in the design of structures in contact with soil masses. This method requires complex constitutive equations on stress strain characteristics of the soil. Similarly, storage facilities for bulk solids may be designed by finite element if the stress-strain behavior or the material to be stored is known.

One problem in using conventional triaxial equipment for determining the stress histories of particulate materials is that the equipment is designed to evaluate soil material at stress ranges much higher than the stresses which exist in other bulk solid storage facilities. A second problem is that the confining stress used in such equipment is often applied via an incompressible liquid which imparts a hydrostatic variation in stress along the length of the specimen. Although this variation may be negligible in soil mechanics applications, it can introduce serious errors in the case of other bulk solids. A final problem is that the individual particle sizes of other particulate materials, in particular agricultural grains, are much larger than those of soil. The size differences require a test cell which allows for accurate measurements of low stress levels while using a large specimen to minimize the effects of individual particle behavior.

When conventional triaxial testing equipment is used in conducting zero lateral strain tests, a measuring device, such as a caliper, is placed around the circumference of the test specimen. Alternatively, complicated equations are used to calculate the volume change in the triaxial cell. The lateral strain measuring device has the limitation that it measures strain only at the diameter where the device is placed on the specimen and as such, ignores strains above and below the device. Also, the lateral strain measuring device applies small confining stresses to the specimen which produce misleading results when deformable particulate materials are being tested.

Therefore, it is a primary objective of the present invention to provide an apparatus for determining the stress-strain relationships of particulate material.

It is a further objective of the present invention to provide an apparatus capable of yielding accurate results when performing zero lateral strain tests constant volume tests, and constant lateral stress tests on particulate material.

It is a further objective of the present invention to provide an apparatus for performing zero lateral strain tests on particulate material without a circumferential strain measuring device or complicated and lengthy calculations.

It is a further objective of the present invention to provide an apparatus for conducting stress-strain tests on particulate material in which the confining stresses are applied by use of compressed air.

It is a further objective of the present invention to provide an apparatus for testing the stress-strain relationships of particulate material that is easy to use and provides accurate results.

SUMMARY OF THE INVENTION

The present invention relates to a triaxial cell apparatus designed for conducting constant lateral stress tests, constant volume tests, and zero lateral strain tests on particulate material at low stress levels. The apparatus comprises a frame, a transparent cylindrical cell mounted on the frame, a flexible cylindrical specimen cell mounted concentrically within the transparent cell, a piston assembly adapted to apply vertical axial forces on the specimen cell and having the same cross-sectional area as the specimen cell, and a mechanical means for activating the piston. A mercury manometer is in communication with both the transparent cell and the specimen cell so that the pressure may be measured and regulated. A volume monitor consisting of a horizontal mercury-filled capillary tube mounted on a scale is in communication with the specimen and transparent cells so as to detect small volume changes within the cells. Also in communication with the specimen cell is a volumeter which also measures volume changes of the material within the specimen cell. A control panel allows the pressure within the transparent cell or within the specimen cell to be increased or decreased as needed in each test.

A constant lateral stress test can be performed upon the material within the specimen cell by applying a compressive or a tensile force to the specimen cell while maintaining the pressure within the transparent cylinder and venting the pressure within the specimen cell to the volumeter. The change in volume of the specimen can be measured by a scale on the volumeter.

A constant volume test can be conducted on the specimen by applying a compressive or a tensile force to the specimen cell while decreasing or increasing the pressure within the transparent cell such that the volume monitor, which is in communication with the specimen cell, maintains a constant reading.

A zero lateral strain test can be performed by applying a compressive or tensile force to the specimen cell while increasing or decreasing the pressure within the specimen cell such that the reading on the volume monitor, which is in communication with the transparent cell, is maintained constant. The change in pressure in the specimen cell may be measured with the mercury manometer.

BRIEF DESCRIPTION OF THE DRAWINGS

FIG. 1 is a perspective view of the triaxial test apparatus.

FIG. 2 is a front elevation sectional view of the transparent cell and the specimen cell as mounted on the frame.

FIG. 3 is a schematic showing the connections of the various pressure and volume measuring devices.

FIG. 4 is a top plan view of the volumeter.

FIG. 5 is a front elevation sectional view of the volumeter taken along line 5—5 of FIG. 4.

DETAILED DESCRIPTION OF THE DRAWINGS

The triaxial cell particulate material testing apparatus is generally designated by the numeral 10. The numeral 12 generally represents the frame of the apparatus. A control panel 14 permits different tests to be conducted on the material by putting the various volume and pressure measuring devices, mercury manometer 16, volume monitor 18, or volumeter 20, in communication with the testing apparatus.

Frame 12 of the device consists of a base 22, top members 24, crossbar 26 spanning between top members 24, and upright posts 28 extending between base 22 and top members 24.

A housing 30 positioned below base 22 houses a conventional worm wheel and worm (not shown) including a drive shaft (not shown) which is in mechanical communication with a hand crank 32 or an electric motor (not shown). The worm wheel and worm are also in operative communication with a screw jack ram 34 having a threaded shaft 36 and a support ram 38. Screw jack ram 34 can be raised and lowered through the worm wheel and worm arrangement by hand crank 32 or the electric motor.

Mounted above and adjacent to support ram 38 is a cylindrical cell 40 having a bottom plate 42, a top plate 44 and a transparent wall 46. Intergrally connected to bottom plate 42 are short upright members 48 adapted to receive threadably upright posts 50 which extend through top plate 44 and are secured by locked wing nuts 52. An airtight seal is provided for transparent cell 40 by tightening wing nuts 52 and posts 50 in short upright members 48.

Concentrically mounted within transparent cell 40 is the specimen cell 54 which has a lower end platen 56, an upper end platen 58, and a flexible membrane wall 60. Wall 60 extends around lower end platen 56 and upper end platen 58 and is sealed thereto by O-rings 62.

A cylinder piston having the same diameter as speciman cell 54 is generally designated by the numeral 64 and comprises a lower plate 66 and a rigid wall 68. Attached to and extending upwardly from lower plate 66 is a shaft 70 which extends through crossbar 26 and is held in place by a conventional thumb screw 72. Top plate 44 of transparent cell 40 has a hole through it sufficiently large to permit piston 64 to move into cell 40. An appropriate seal is provided in the hole in top plate 44 to provide an airtight seal with wall 68 of piston 64. At the top end of piston wall 68 is a piston guide plate 74 which is held in place by elongated bolts 76 which pass through plate 74 and are threaded into top plate 44 of transparent cell 40. Guide plate 74 has a hole that permits shaft 70 to be slidably received therein.

The design of the present apparatus is such that when the jack ram 34 is raised by hand crank 32 or by an electric motor, the support ram 38 forces the entire apparatus from bottom plate 42 of transparent cell 40 to piston guide plate 74 upwardly, except for lower plate 66, piston wall 68 and shaft 70, which remain stationary. Four dog clamps 78 are secured to bottom plate 42 by bolts 80 so that the process may be reversed to lower the entire device between bottom plate 42 and guide plate 74 while shaft 70, piston wall 68 and lower plate 66 of piston 64 remain stationary. A displacement gauge 82 is in communication with piston 64 through arm 84 attached to piston wall 68 and gauge rod 86 so as to measure the linear displacement of piston 64 with respect to the transparent cell 40.

It is understood that the test apparatus of the present invention could alternatively be designed so that the transparent cell 40 remains stationary while the piston 64 is actuated to move upwardly and downwardly with respect to cell 40 without detracting from the present invention.

Attached to upper end platen 58 of specimen cell 54 is a pole piece 88 which in turn is in contact with an electromagnet 90. A conventional proving ring 92 is connected at its lower end to electromagnet 90 and at its upper end to lower plate 66 of piston 64. The proving ring 92 measures axial load and is placed within transparent cell 40 to avoid the problem of piston friction, which is significant in a conventional triaxial test machine, but is greatly magnified when the piston has the same cross-sectional area as the specimen cell, as in the present device. The proving ring is rigid in comparison to the material being tested, so deflections of the ring do not introduce serious errors in vertical strain measurement and in volume monitoring. A gauge 94 on proving ring 92 measures such deflection. Switch 91 on control panel 14 activates the electromagnet 90 so that tensile forces may be applied to the specimen cell 54.

The mercury manometer 16 measures the differential pressure in transparent cell 40 and specimen cell 54. The mercury manometer 16 has a vertical orientation and comprises a scale 96 and a capillary tube 98 partially filled with mercury. Tube 98 is a continuous tube with one half 100 being a vacuum portion in communication with specimen cell 54 while the other half 102 is a pressure portion in communication with transparent cell 40. Vacuum portion 100 is also in communication with a vacuum pump (not shown) and pressure portion 102 is in communication with an air compressor (not shown). Increased pressure in line 102 is controlled by valve 104 on control panel 14 and may be released by valve 106 on control panel 14. The vacuum in line 100 may be increased through control valve 108 and released by valve 110 of control panel 14. A mercury trap may be provided on lines 100 and 102 in case of mercury overflow resulting from sudden pressure changes.

The volume monitor 18 measures small changes in volume within the specimen cell 54 when the stresses on the cell are changing. Volume monitor 18 comprises a horizontally orientated capillary tube 112 partially filled with mercury which is mounted on a scale 114. A mercury trap 116 at each end of tube 112 prevents an overflow of the mercury. An electrically driven agitator 118 with a hook 120 engaging tube 112 is provided to shake tube 112 slightly so that the mercury within will remain fluid. Agitator 118 is activated by switch 122 of control panel 18 and its speed is controlled by potentiometer 124. The volume monitor 18 may be placed in communication with the specimen cell 54 through valve 126 and volume monitor tube 128. Valve 126 also permits volume monitor 18 to be put into communication with the transparent cell 40 via line 129. A second valve 130 merely vents tube 128 to the atmosphere for initial set up of the apparatus. Valve 126 may be closed if the volume monitor 18 is not needed for a particular test.

Volumeter 20 measures large changes in volumes within the specimen cell 54. Volumeter 20 comprises a container 132 capable of holding water, a floatation guide 134 mounted on container 132, a floatation device 136, which may be merely an inverted thin cup, and a vertical scale 138. Floatation guide 134 has an opening sufficiently large to receive cup 136 so that a small gap 140 is maintained between the wall 142 of the cup and the interior edge 144 of floatation guide 134. Container 132 is filled with water so that the water level at least covers the upper surface 146 of guide 134. By keeping the water at this level, capillary action of the water in gap 140 on cup 136 is prevented. Cup 136 floats on a pocket of air 148. A tube 150 is in communication at one end with the pocket of air 148 and at the other end with the specimen cell 54. Increases or decreases in the volume within the specimen cell 54 cause air to be drawn into or expelled from cell 54, thus causing cup 136 to fall or rise, respectively, with such volume changes being measured by scale 138. Any conventional means such as a valve 152 may be supplied for providing the communication in tube 150 from cup 136 to cell 54.

The apparatus of the present invention can conduct any of the three primary tests used in determining stress paths of particulate material. The constant lateral stress test (standard test) simulates loading of the material into a rigid structure wherein compressive forces are applied to the top of the specimen while the lateral stresses remain constant. In this extension unloading test, tensile forces are applied to the specimen while the lateral stress on the specimen remains constant.

The constant volume test simulates the stress which may occur on bulk solids during unloading. In the constant volume test, the axial and lateral stresses are adjusted to maintain a constant specimen volume.

In the zero lateral strain test, compressive forces are applied to the specimen while the lateral stresses are increased so as to yield zero lateral strain. This test simulates the stresses in particulate materials within a rigid structure when the material is "at rest".

The various forces applied to the specimen in each test may cause the specimen to dilate and increase in volume. This dilation is the shearing between individual particles and the resulting movement of particles over each other. Such an increase in volume causes increased stresses on the confining structure. It is necessary to know the stress and strain parameters of the specimen so that safe structures may be constructed.

The confining stress on the specimen is equal to the pressure difference between the specimen cell 54 and the transparent cell 40. This pressure difference is measured by the differential manometer 16. The confining stress on the specimen may be increased by decreasing the pressure in the specimen cell 54 and/or by increasing the pressure in the transparent cell 40 via the vacuum pump or the air compressor, respectively. The confining stress is applied via a light gas rather than a heavy liquid so as to avoid hydrostatic pressure variations along the length of the specimen.

In operation, the triaxial apparatus of the present invention can be used to run the three separate tests on the particulate material being tested. Each test is conducted until the material fails. In each of the tests the material 154 to be tested is loaded into the specimen cell 54 by removing O-ring 64 from the upper end platen 58 and pealing the flexible membrane 60 from platen 58. A longitudinally split pipe (not shown) may be placed around the cell 54 to aid in the loading so that flexible wall 60 will maintain a cylindrical shape. When the cell is filled, wall 60 is replaced about end platen 58 and the O-ring 62 is put in place to create an airtight seal. A small amount of air is evacuated from specimen cell 54 via vacuum tube 100, valve 108, and the vacuum pump (not shown). When the longitudinally split pipe is removed, cell 54 will maintain its cylindrical shape.

The first test is the standard constant lateral stress test which is used to measure stress-strain characteristics including volume changes within cell 54 as compressive forces are applied to the cell while maintaining a constant confining stress. Hand crank 32 or an electric motor (not shown) is activated so as to raise screw jack ram 34 which in turn will raise the entire apparatus, including bottom plate 42 of transparent cell 40 and piston guide plate 74, upwardly upon shaft 70 while piston 64 remains stationary. Thus, piston 64 moves into the inner space of transparent cell 40. The relative displacement of the piston 64 within cell 40 is measured by gauge 82. Compressive forces are therefore applied to upper end platen 58 of the specimen cell 54 through the linkage of the proving ring 92, the electromagnet 90, and the pole piece 88. As the compressive forces are applied, wall 60 of specimen cell 54 tends to barrel-out. As wall 60 barrels-out, the particles in specimen 154 shear with respect to each other and ride over each other, thus increasing the pore space volume within specimen cell 54. As the volume increases, air is sucked into specimen cell 54 from the air pocket 148 via communicating tubes 150 and 100. The increase in volume can be measured by scale 138 on volumeter 20 as being the change in distance that the cup 136 falls. During this standard test the confining stress is held constant by merely venting cell 54 to the atmospheric pressure on cup 136. Axial stresses are measured with proving ring 92 and strains with gauge 82. Volume monitor 18 is not in communication with specimen cell 54 during this test.

In the constant volume test the pore space volume within specimen cell 54 is held constant. This could be done by maintaining cup 136 of volumeter 20 at a steady height on scale 138. It is more desirable, however, to disengage volumeter 20 and use the volume monitor 18 which is more sensitive to volume changes. Volume monitor 18 is in communication with cell 54 via valve 126 and tube 128. Movement of the mercury within tube 112 which is in communication with specimen cell 54 via lines 128 and 100 indicates a change in volume within specimen cell 54. Therefore, it is necessary to keep the mercury bead stationary along the scale 114 of the monitor 18 by adjusting the confining air pressure. In the constant volume test, the vertical and/or lateral stresses may be increased or decreased. To decrease the vertical stress, the electromagnet 90 is activated so that piston 64 can be withdrawn from transparent cell 40. Thus, axial stresses which are less than the lateral stresses are applied to specimen cell 54. As the axial stresses are reduced, wall 60 will tend to bow-in and again the particles will shear with respect to each other and move over each other so as to tend to increase the pore space volume of specimen 154. The pressure is decreased in the transparent cell 40 via valve 106. The change in confining stress can be measured on the manometer 16. This test simulates the unloading stresses upon particulate material, such as unloading grain from a silo.

The third test is the zero lateral strain test which would represent the packing down of particulate material within a rigid container. In this test, the vertical stress and lateral stress are increased so as to yield a zero lateral strain. The piston 64 enters transparent cell 40 to apply the axial stress. The confining stress is applied by partially evacuating the air in the specimen cell 54 while maintaining the cell 40 air at atmosphere pressure. The diameter of specimen cell 54 remains constant although its volume changes. Zero lateral strain of the specimen 154 is maintained indirectly by connecting the volume monitor 18 to the transparent cell 40, via valve 126 and line 129, and by adjusting the partial vacuum in the specimen cell 54, such that the mercury bead in tube 112 remains stationary. Because the cross-sectional area of the piston is the same as that of cell 54, the volume of cell 54 is changed in the same ratio as the decrease in length of the cell 54 caused by the entry of piston 64 into cell 40. The volume of air within cell 40 is held constant via the hookup with the volume monitor 18, while the changes in lateral stresses on wall 60 of cell 54 are measured by the differential manometer 16.

By conducting the various tests possible with the present apparatus, the stress histories of particulate materials can be determined so as to aid in the design of the material confining structures.

It can be seen that at least all of the stated objectives are accomplished by the apparatus of the present invention.

What is claimed is:

1. A triaxial particulate material testing apparatus comprising:
   a frame,
   a cylindrical outer cell having a top, a bottom, and a rigid side wall mounted on said frame,
   a concentric cylindrical inner specimen cell having a top, a bottom, and a flexible side wall mounted within said outer cell for receiving the material to be tested,
   means for supplying a compressible fluid to said inner and outer cells,
   a pressure measuring means adapted to measure the pressure in said inner and outer cells,
   at least one volume measuring means adapted to measure the volume changes in said inner and outer cells,
   a piston means positioned within said outer cell and adapted to apply compressive and tensile forces on said inner cell,
   a piston actuation means, and
   a control means adapted to control volume and pressure changes within said inner and outer cells.

2. The apparatus of claim 1 wherein said pressure measuring means includes a mercury manometer having a vacuum hose in communication with said inner cell and a pressure hose in communication with said outer cell, said vacuum and pressure hoses also being in communcation with a vacuum pump and air compressor, respectively.

3. The apparatus of claim 1 where a first volume measuring means includes a volume monitor having a mercury tube mounted on a horizontal scale, a hose in communication at one end with said mercury tube and selectively in communication at the other end with either said inner cell or said outer cell or neither of said cells, and an agitator to keep the mercury in said mercury tube fluid, said scale measuring the displacement of the mercury resulting from air volume changes within said inner and outer cells.

4. The apparatus of claim 1 wherein a second volume measuring means includes a volumeter comprising a container filled with water, a float guide mounted in said container, an inverted cup floating freely within said float guide on a pocket of air, and a hose in communication at one end with said pocket of air beneath said cup and at the other end with said inner cell, and a vertical scale attached to said volumeter for measuring the rise or fall of said cup resulting from decreases or increases, respectively, in volume within said inner cell.

5. The apparatus of claim 1 wherein said piston means comprises a cylinder having a top, a bottom and a side wall, said cylinder being slidably mounted on a shaft connected to said frame and being adapted to move into and out of said outer cell and having a diameter equal to that of said inner cell.

6. The apparatus of claim 5 wherein said piston means is connected at said bottom of said cylinder to a proving ring which in turn is connected to an electromagnet attached to said top of inner cell.

7. The apparatus of claim 6 wherein said piston means provides compressive forces to said inner cell when said cylinder moves into said outer cell and said piston means provides tensile forces on said inner cell when said electromagnet is activated and said cylinder moves out of said outer cell.

8. The apparatus of claim 7 wherein the cross-sectional area of said piston means equals the cross-sectional area of said inner cell.

9. The apparatus of claim 8 wherein said piston actuation means raises and lowers said outer cell therby moving said piston means into and out of said outer cell respectively.

10. The apparatus of claim 1 wherein said control means permits different tests to be conducted on said material for determining the stress histories of said material, said tests including a constant volume test, a constant lateral stress test, and a zero lateral strain test.

11. A method of determining stress histories of a particulate material sample to be tested in a tiraxial testing apparatus comprising a frame, an airtight rigid cylindrical outer cell mounted on said frame, an airtight flexible cylindrical inner specimen cell mounted concentrically within said outer cell, a pressure measuring means adapted to measure the pressure in said inner and outer cells, a volume measuring means adapted to measure volume changes within said inner cell, a piston means positioned within said outer cell and adapted to apply compressive and tensile forces on said inner cell, a piston actuation means, and a control means for regulating the quantity of a compressible fluid within said inner and outer cells such that volume and pressure changes within said cells can be controlled, said method comprising:
   loading said material to be tested into said inner cell,
   coupling said inner cell to said volume measuring means, activating said piston actuation means,
   maintaining constant lateral stress on said material in said inner cell by regulating the quantity of said compressible fluid within said inner cell,
   further increasing said force on said inner cell until said material fails,
   measuring the volume change of said material in said inner cell with said volume measuring means from initial loading to failure of said material.

12. The method of claim 11 whereby compressive or tensile force is applied to said material in said inner cell by said piston means moving into or out of said outer cell, respectively.

13. The method of claim 11 whereby constant lateral stress is maintained on said material in said inner cell by venting said inner cell to the atmosphere.

14. A method of determining stress histories of a particulate material sample to be tested in a triaxial testing apparatus comprising a frame, an airtight rigid cylindrical outer cell mounted on said frame, an airtight flexible cylindrical inner specimen cell mounted concentrically within said outer cell, a pressure measuring means adapted to measure the pressure in said inner and outer cells, a volume measuring means adapted to measure volume changes within said inner cell, a piston means positioned within said outer cell and adapted to apply compressive and tensile forces on said inner cell, a piston actuation means, a means for increasing and decreasing the pressure within said outer cell, and a control means for regulating the quantity of a compressible fluid within said inner and outer cells such that volume changes within said cells can be controlled, said method comprising: loading said material to be tested into said inner cell, coupling said inner cell to said volume measuring means, activating said piston actuation means, applying forces to said inner cell, maintaining constant volume of said material in said inner cell by regulating the quantity of compressible fluid within said outer cell, further increasing said forces until said material fails, measuring the pressure difference between said inner and outer cells with said pressure measuring device from initial loading to failure of said material.

15. The method of claim 14 whereby compressive or tensile force is applied to said material by the movement of said piston means into or out of said outer cell, respectively.

16. The method of claim 14 whereby said constant volume of said material is maintained by increasing or decreasing the pressure within said outer cell.

17. A method of determining stress histories of a particulate material sample to be tested in a triaxial testing apparatus comprising a frame, an airtight rigid cylindrical outer cell mounted on said frame, an airtight flexible cylindrical inner specimen cell mounted concentrically within said outer cell, a pressure measuring means adapted to measure the pressure in said inner and outer cells a volume measuring means adapted to measure volume changes within said outer cell, a piston means positioned within said outer cell and adapted to apply compressive and tensile forces on said inner cell, a piston actuation means, a means for increasing or decreasing the vacuum within said inner cell, and a control means for regulating the quantity of a compressible fluid within said inner and outer cells such that volume and pressure changes within said cells can be controlled, said method comprising:

loading said material to be tested into said inner cell, coupling said outer cell to said volume measuring means, activating said piston actuation means, applying force to said inner cell, maintaining zero lateral strain on said material within said inner cell by regulating the quantity of compressible fluid within said cells, further increasing said forces until said material fails, measuring the pressure difference between said inner and outer cells from initial loading to failure of said material.

18. The method of claim 17 whereby said compressive or tensile force is applied to said material by said piston means moving into and out of said outer cell, respectively.

19. The method of claim 17 whereby zero lateral strain on said material is maintained by decreasing the pressure within said inner cell and venting said outer cell to the atmosphere.

\* \* \* \* \*